United States Patent [19]

Strope

[11] 4,234,454

[45] Nov. 18, 1980

[54] DIOLEFIN DIMERIZATION CATALYST AND METHOD FOR PRODUCING NITROSYL HALIDES OF IRON TRIAD METALS

[75] Inventor: Daniel J. Strope, Bartlesville, Okla.

[73] Assignee: Phillips Petroleum Company, Bartlesville, Okla.

[21] Appl. No.: 61,123

[22] Filed: Jul. 27, 1979

Related U.S. Application Data

[62] Division of Ser. No. 964,326, Nov. 29, 1978, Pat. No. 4,181,707, which is a division of Ser. No. 817,471, Jul. 20, 1977, Pat. No. 4,144,278.

[51] Int. Cl.$^3$ .................... B01J 31/22; B01J 31/24; B01J 27/24
[52] U.S. Cl. .................... 252/429 R; 252/429 A; 252/429 B; 252/430; 252/431 N; 252/431 P; 252/438
[58] Field of Search .................... 423/386; 252/429 R, 252/429 A, 429 B, 430, 438, 431 N, 431 P

[56] References Cited

U.S. PATENT DOCUMENTS

| | | | |
|---|---|---|---|
| 3,377,397 | 4/1968 | Maxfield | 585/369 |
| 3,427,365 | 2/1969 | Maxfield | 252/431 P X |
| 3,448,129 | 6/1969 | Maxfield | 252/431 N X |
| 3,481,710 | 12/1969 | Maxfield | 260/606.5 P X |
| 3,655,793 | 4/1972 | Myers | 585/369 |
| 3,767,593 | 10/1973 | Myers | 252/438 X |
| 3,917,730 | 11/1975 | Tkatchenko | 252/438 X |
| 3,957,894 | 5/1976 | Saeki et al. | 585/369 |

FOREIGN PATENT DOCUMENTS

1093093  11/1960 Fed. Rep. of Germany ...... 252/429 A

OTHER PUBLICATIONS

King, *Organometallic Synthesis,* Academic Press, (1965), pp. 165–168.

*Primary Examiner*—Patrick Garvin

[57] ABSTRACT

A diolefin dimerization catalyst is disclosed which is formed by contacting components consisting essentially of at least one nitrosyl metal halide and at least one of elemental manganese, zinc, or tin. Also new methods for preparing nitrosyl halides of iron triad metals are disclosed.

8 Claims, No Drawings

DIOLEFIN DIMERIZATION CATALYST AND METHOD FOR PRODUCING NITROSYL HALIDES OF IRON TRIAD METALS

This application is a division of application Ser. No. 964,326, filed Nov. 29, 1978, now U.S. Pat. No. 4,181,707, which was a division of application Ser. No. 817,471, filed July 20, 1977, now U.S. Pat. No. 4,144,278.

This invention relates to the preparation of nitrosyl halides of an iron triad metal, i.e., iron, cobalt or nickel. In one aspect this invention relates to methods for preparing ligand-containing nitrosyl halide complexes of iron, cobalt, and nickel. In yet another aspect this invention relates to the dimerization of conjugated dienes with a catalyst employing an iron triad metal nitrosyl halide. In yet a further aspect, this invention relates to a novel composition of matter comprising a diolefin dimerization catalyst employing an iron triad metal nitrosyl halide.

While nitrosyl halides of iron, cobalt and nickel are known compounds, many prior art processes for synthesizing these materials are very tedious and time consuming and the yield of the desired compounds are quite low. An example is the process disclosed by Walter Hieber and Reinhard Nast, "Chemical Abstracts", volume 35 (1941), column 2807-2808. In that process a compound of the formula Ni(NO)I was prepared by the solid phase reaction of nickel iodide and zinc dust with nitric oxide. U.S. Pat. No. 3,481,710 disclosed an improved process for forming iron triad metal nitrosyl halides by reacting the metal dihalides with nitric oxide and the respective elemental iron triad metal or zinc. The present invention provides a new and simplified procedure for the production of iron triad metal nitrosyl halides.

Therefore, one object of this invention is to provide a new, efficient method for the preparation of iron triad metal nitrosyl halides. A further object of this invention is to provide a method for the production of nitrosyl halides from readily available, easily handled materials. It is another object of this invention to provide a method for the production of ligand-containing nitrosyl halide complexes. It is yet another object of this invention to provide a method for the synthesis of nitrosyl metal halides and complexed derivatives thereof in good yields and of sufficient purity for use as catalyst components. Another object of this invention is to provide a new and improved method for dimerizing conjugated dienes. A still further object of this invention is to provide a new and improved catalyst system for the dimerization of conjugated dienes.

Other aspects, objects, and several advantages of this invention will be apparent to one skilled in the art from a reading of this disclosure and the appended claims.

PRODUCTION OF NITROSYL HALIDES

In accordance with one embodiment of this invention, iron triad metal nitrosyl halides having the formula $[Fe(NO)_2X]_y$, $[Co(NO)_2X]_y$, or $[Ni(NO)X]_y$, are prepared from the corresponding metal dihalide wherein X is either chlorine, bromine, or iodine, and y is 1 or 2 for Co and Fe and 1,2,3, or 4 for Ni by the reaction of the metal dihalide with an alkali metal nitrite in the presence of the corresponding elemental iron triad metal and/or elemental zinc in a liquid in which the metal dihalide is at least partially soluble and under reaction conditions suitable for yielding said nitrosyl iron triad metal halide.

In accordance with another embodiment of the present invention, nitrosyl iron halides and nitrosyl cobalt halides having the formulas as set forth above are prepared by a two-step process involving (1) reacting, in a liquid in which the corresponding iron triad metal dihalide is at least partially soluble, the corresponding ferric halide or cobaltic halide with the corresponding elemental iron triad metal and/or elemental zinc under conditions suitable for producing a product mixture containing the corresponding iron triad metal dihalide and (2) reacting at least a portion of this iron triad metal dihalide with an alkali metal nitrite under reaction conditions suitable for yielding said corresponding nitrosyl iron triad metal halide.

In accordance with another embodiment of this invention, nitrosyl nickel halides, having the formula $[Ni(NO)X]_y$, are prepared from the corresponding nickel dihalide wherein X is either chlorine, bromine, or iodine, and y is 1,2,3 or 4, by the reaction of the nickel dihalide with an alkali metal nitrite in the presence of elemental nickel and/or elemental zinc in a liquid in which the nickel dihalide is at least partially soluble and under reaction conditions suitable for yielding said nitrosyl nickel halide.

In accordance with yet another embodiment of the present invention, ligand-containing iron triad metal nitrosyl halides of the formula $Fe(NO)_2(L)X$, $Ni(NO)(L)X$ or $Co(NO)_2(L)X$ are prepared from the corresponding metal dihalide wherein X is either chlorine, bromine or iodine by the reaction of the metal dihalide with an alkali metal nitrite in the presence of the corresponding elemental iron triad metal and/or elemental zinc and at least one compound (L) which forms ligands with iron triad metal nitrosyl halides, said reaction being conducted under conditions such that said ligand-containing iron triad metal nitrosyl halide is produced.

A still further embodiment of the present invention is the production of ligand-containing iron triad metal nitrosyl halides of the formula $Fe(NO)_2(L)X$ or $Co(NO)_2(L)X$ by the reaction of the corresponding metal dihalide wherein X is either chlorine, bromine, or iodine by the reaction of the metal dihalide with an alkali metal nitrite in the presence of at least one compound (L) which forms ligands with iron triad metal nitrosyl halides, said reaction being conducted under conditions such that ligand-containing iron triad metal nitrosyl halide is produced.

In preparing the nitrosyl halides, any solvent for the iron triad metal dihalide can be employed which does not prevent the desired reaction. Specific examples of solvents suitable for use in preparing the nitrosyl halides in accordance with this invention include saturated mono- and polyethers, which can be cyclic or acyclic and have from 3 to 20 carbon atoms per molecule and aromatic hydrocarbons having from 6 to 8 carbon atoms per molecule. The preferred solvents are those which have boiling points in the range of about 50° to about 100° C., or whose boiling points can be adjusted to that range by convenient manipulation of the reaction pressure. Any suitable amount of solvent can be employed, generally about 5 to about 50 parts of solvent is used per part of metal dihalide, by weight.

Some examples of suitable solvents are ethyl ether, methyl ether, butyl ether, methyl ethyl ether, tetrahydrofuran, p-dioxane, diglyme(diethylene glycol dimethyl ether), diethoxyethane, triglyme(triethylene glycol dimethyl ether), decyl cyclopropyl ether, 2-ethylhexyl dodecyl ether, benzene, toluene, o-xylene, and the like and mixtures of any two or more thereof. Ethers are presently the preferred solvents, tetrahydrofuran being particularly desirable.

The elemental iron triad metal and elemental zinc are preferably employed in a finely divided powder form. Generally, it is suitable to employ elemental metal having average particle diameter in the range of about 0.037 mm to about 25 mm, preferably about 0.074 to about 0.25 mm.

Any suitable alkali metal nitrite can be reacted with the metal dihalides according to the embodiments described above. Examples of suitable alkali metal nitrites include lithium nitrite, sodium nitrite, potassium nitrite, rubidium nitrite, and cesium nitrite. Mixtures of any two or more of alkali metal nitrites may also be utilized if so desired.

In forming the ligand-containing iron triad metal nitrosyl halides, the compound (L) can be any compound which forms ligands with iron triad metal nitrosyl halides. Examples of suitable ligand-forming compounds are those of the formulas

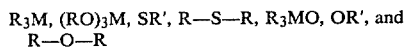

wherein each R is individually selected from the group consisting of hydrocarbyl aromatic radicals, hydrocarbyl aliphatic radicals, halo-substituted hydrocarbyl aromatic radicals, halo-substituted aliphatic hydrocarbyl radicals, alkoxy-substituted hydrocarbyl aromatic radicals and alkoxy-substituted aliphatic hydrocarbyl radicals, having up to about 20 carbon atoms; wherein R' is a divalent saturated or olefinically unsaturated hydrocarbyl radical having 3 to 7 carbon atoms; and wherein M is phosphorus, antimony, or arsenic. When such ligand-forming materials are present in the reaction zone, the iron triad metal products have formulas $Fe(NO)_2(L)X$, $Ni(NO)(L)X$, or $Co(NO)_2(L)X$ where (L) represents the ligand-forming material used.

Some specific examples of suitable ligand-forming compounds are tributylphosphine, triphenylphosphine, triphenylphosphine oxide, trioctyl phosphite, tribenzylarsine, triphenyl stibonite, tricyclopentyl arsonite, tris(4-bromophenyl)phosphite, trieicosylstibine, diphenylmethylphosphine, tris(2,4,6-trimethoxybenzyl)phosphine, methyl sulfide, ethyl sulfide, methyl isobutyl sulfide, thiophene, and the like, and mixtures of any two or more thereof. Where more than one ligand-forming compound is employed, the ligand-forming compounds which result in the most stable ligands will generally provide the predominant ligand in the ligand-containing iron triad nitrosyl halide.

It should be noted that if the solvent employed in the present invention is a ligand-forming compound, in order to recover the corresponding iron triad metal nitrosyl halide, the ligand will have to be removed by techniques known in the art. For example, if ethers are utilized in the reaction of this invention as a suitable solvent, the product obtained can contain ether ligands. The ether ligand-containing iron triad metal nitrosyl halide can be readily converted to the nonligand-containing iron triad metal nitrosyl halide by the evaporation of the ether.

Any amounts of reactants can be employed which will result in the production of some of the desired product.

In the embodiments of the invention in which ferric halide or cobaltic halide are used as starting materials, the stoichiometry for the complete conversion of trihalide to dihalide requires that $\frac{1}{2}$ mole of elemental iron triad metal or elemental zinc be employed for every mole of trihalide to be reduced. Although less than such a stoichiometric amount can be used, such a procedure would result in poorer yields of the dihalide and accordingly poorer yields of the corresponding iron triad metal nitrosyl halide. It is therefore presently preferred that the amount of elemental iron triad metal and/or elemental zinc be at least the stoichiometric amount. It is especially preferable if the amount of the elemental iron triad metal and/or elemental zinc employed is greater than the stoichiometric amount in order to provide substantially complete conversion of the iron triad trihalide to the dihalide. Where excess elemental iron triad metal and/or elemental zinc is employed in the reduction step, it is not necessary that separation of this excess from the products be made before the subsequent reaction with the alkali metal nitrite to obtain the corresponding metal nitrosyl halide since that reaction can also be carried out in the presence of elemental iron triad metal and/or elemental zinc. (It should be noted, however, that the presence of elemental iron triad metal and/or elemental zinc is not essential for the production of the corresponding metal nitrosyl halide when iron dihalide or cobalt dihalide is reacted with the alkali metal nitrite.)

While, as indicated in the preceding paragraph, zinc can be employed to accomplish the reduction of the ferric or cobaltic halides, better yields can be achieved by conducting such reduction with the respective elemental iron triad metal because at least a portion of the elemental iron triad metal can be converted into additional ferrous halide or cobaltous halide.

The amount of alkali metal nitrite reacted with the iron triad metal dihalide can be any amount which results in the production of iron triad metal nitrosyl halide. Generally, the molar ratio of alkali metal nitrite to iron triad metal dihalide will be in the range of about 0.1/1 to about 20/1. Higher or lower ratios could be employed but with obvious economic disadvantages. Preferably the ratio is in the range of about 0.5/1 to about 6/1. It is especially preferred for the amount of alkali metal nitrite to be since that at least about one-half of the iron triad metal dihalide is converted to the corresponding nitrosyl metal halide.

As indicated above, when ferrous or cobaltous halide is reacted with alkali metal nitrite, elemental iron triad metal and/or elemental zinc need not be present for the production of the corresponding iron triad metal nitrosyl halide. With nickel dihalide, however, in order to obtain nickel nitrosyl halide, elemental nickel and/or elemental zinc must be present when the nickel dihalide is reacted with the alkali metal nitrite. Any amount of the elemental nickel and/or zinc can be employed which will allow the production of the nickel nitrosyl halide. Generally, the molar ratio of the elemental metal to the nickel dihalide is in the range of about 0.1/1 to about 10/1, preferably 0.5/1 to about 10/1.

The amount of ligand-forming compound, when employed, can be any amount which results in the production of ligand-containing iron triad metal nitrosyl halide. For economic reasons generally the molar ratio of ligand-forming compound to iron triad metal dihalide is in the range of about 0.1/1 to about 5/1, preferably about 0.5/1 to about 1.2/1. To assure maximum yield, it is preferred that the molar ratio of ligand-forming compound to iron triad metal dihalide be at least about 1/1.

The above reactions can be carried out at any temperature which do not prevent the productin of the nitrosyl metal product. For example, the conversion of ferric or cobaltic halides to dihalides can be carried out at any temperature sufficient to produce such dihalides. Generally, this would be a temperature in the range of about 25° to about 125° C., and preferably about 50° to about 100° C. The reaction of the alkali metal nitrite and iron, cobalt or nickel metal dihalides (with or without ligand-forming compound) can be carried out at any temperature sufficient to produce the corresponding iron triad metal nitrosyl halide. Generally, this could be a temperature in the range of about 50° to about 200° C., preferably about 70° to about 150° C. It is often convenient to carry out the reactions in refluxing diluent, thus the choice of the diluent may determine the reaction temperature utilized. Any suitable pressure can also be employed in the above reactions. Generally, in the reaction of the alkali metal nitrite with the iron triad metal dihalide pressures in the range of about 25 to about 400 psig are suitable. While the rate of the reaction was generally greater at temperatures above 60° C., there was no observable pressure effect.

The reaction time for preparing the dihalides, the iron triad metal nitrosyl halides, and the ligand-containing iron triad metal nitrosyl halides is any length of time sufficient to provide a yield of the desired product. The selection of suitable reaction time is well within the skill of those in this art. Generally, the ferric or cobaltic halides can be converted to the corresponding dihalides in less than one hour, although longer times can be employed if desired.

In the case of ferric halide reduction, the extent of reduction can be easily determined by the change in color from orange color (ferric) to a gray color (ferrous). Thus, when starting with ferric halide one can proceed to the second step of the reaction when the color of the reaction mixture has turned gray. It is not, however, necessary that all the ferric or cobaltic halide be reduced to dihalide before the second step is initiated. Generally, the reaction of the alkali nitrite and the iron triad metal dihalide can be completed in less than one hour. Here again, however, longer times can be employed.

Since the nitrosyl metal halides produced according to this invention are quite sensitive to water and oxygen, the amount of water and oxygen present should be below that which would prevent the formation of the iron triad metal nitrosyl halides or their ligand-containing counterparts. It is therefore preferred that the reaction be carried out under an inert atmosphere, for example nitrogen, argon, or helium, and that the substances employed be at least substantially water-free. It is also preferable to conduct the reactions with stirring which will achieve intimate contact of all the reaction ingredients.

The nitrosyl metal halides of iron, cobalt and nickel and their ligand-containing counterparts have utility as catalyst components for the conversion of olefins or diolefins in reactions such as oligomerization, polymerization and the like. In particular, the nitrosyl iron halides prepared according to the instand invention have utility in the dimerization of conjugated diolefins, i.e., 1,3-butadiene, isoprene and mixtures thereof, when combined with a suitable reducing agent according to the procedures taught in U.S. Pat. No. 3,377,397, Perry L. Maxfield. Also, the ligand-containing nitrosyl nickel halides prepared in accordance with the present invention have utility in the dimerization of monoolefins in accordance with the teachings of U.S. Pat. No. 3,427,365, Perry L. Maxfield.

DIMERIZATION REACTION AND DIMERIZATION CATALYST

In accordance with another embodiment of the instant invention, the combination of (1) at least one nitrosyl metal halide selected from the group of nitrosyl halides having the formula $[Fe(NO)_2X]_y$, $[Co(NO)_2X]_y$, $[Ni(NO)S]_y$, $Fe(NO)_2(L)X$, $Ni(NO)(L)X$, and $Co(NO)_2(L)X$, as defined above, with (2) at least one elemental metal selected from manganese, tin, and zinc provides a novel catalyst system for the dimerization of conjugated diolefins. The use of elemental metals such as manganese, zinc, or tin instead of the organometallic compounds used in prior art dimerization processes offers several distinct advantages. For example, zinc, manganese, and tin metal is more easily handled than the pyrophoric and extremely air and water sensitive organometallics used in prior art dimerizations. Furthermore, the metals manganese, zinc, and tin are much less expensive than the organometals which are difficult to prepare and in many instances, difficult to store in a useable condition. Preferably the manganese, zinc and tin are employed in the form of finely divided metal powder. Generally, it is suitable to employ the elemental metal in the form of particles having an average particle diameter in the range of about 0.37 mm to about 25 mm, preferably about 0.074 to about 0.25 mm.

The dimerization catalyst system mentioned in the previous paragraph is suitable for dimerizing a large number of conjugated diolefins. Typically the catalyst system can be utilized in the dimerization of one or more acyclic conjugated dienes having from 4 to 12 carbon atoms per molecule. Examples of such suitable conjugated dienes are isoprene, 1,3-butadiene, piperylene, 2,3-dimethyl-1,3-butadiene, 1,3-hexadiene, 2,4-octadiene, 2-methyl-1,3-pentadiene, 4-ethyl-1,3-decadiene, and the like, and mixtures of any two or more thereof.

It should be noted that generally the crude product mixture resulting from the preparation of the nitrosyl halide derivative cocatalyst in accordance with this invention can be employed directly in the dimerization process. That is, it is not generally necessary to use the nitrosyl halide derivative cocatalyst in its isolated form. Occasionally though, if the product mixture contains certain of the ligand-forming compounds in too great an extent, the ligand-forming compounds may exert an inhibiting effect upon the dimerization. Such has been noted for a crude reaction mixture containing excess triphenyl phosphine.

Preferably, a diluent or solvent, substantially nonreactive with the other components, is employed in the dimerization reaction. Particularly preferred diluents include saturated mono- and polyethers, which are cyclic or acyclic and have from 3 to 20 carbon atoms per molecule and aromatic hydrocarbons having 6 to 8 carbon atoms per molecule. Examples of suitable diluents include pentane, heptane, cyclohexane, benzene, toluene, xylene, chlorobenzene, methylene chloride, tetrahydrofuran, and the like, and mixtures of any thereof.

The above-described first and second catalyst components can be combined in any amounts which result in an active catalyst, generally they are combined, for use in this invention, in proportions such that the mole ratio of the aforementioned elemental metal to the nitrosyl metal halide is in the range of about 0.75/1 to about 50/1, and preferably in the range of about 1/1 to about 30/1. Any catalytic amount of the nitrosyl metal halide containing catalyst can be employed. The mole ratio of diolefin to the nitrosyl metal halide for practical purposes is generally in the range of about 50/1 to about 50,000/1, preferably about 500/1 to about 5,000/1.

The order in which the catalyst components and the diolefin feed are combined is not considered to be critical. Of course, since the nitrosyl metal halides are sensitive to both oxygen and water, suitable steps should be taken to minimize the effects of those materials. Preferably the catalyst components and the diolefin feed are combined under an inert atmosphere and the inert atmosphere is maintained during the dimerization. A suitably inert atmosphere can be provided by gases such as nitrogen, argon, etc. Also it is preferred that the diolefinic feed be free of any deleterious amounts of materials which act as catalyst poisons, such as oxygen, water, allenes, and acetylenes.

According to this invention, the dimerization occurs when the diolefin is contacted with the catalyst at a temperature which allows production of the dimer. Generally, suitable temperatures are in the range of about 0° to about 100° C., and preferably are in the range of about 20° to about 80° C. The dimerization can be carried out at any convenient pressure which is sufficient to maintain the reaction mixture in a substantially liquid state. Generally, pressures ranging from 0 to about 1,000 psig can be used. The contact time will vary according to the efficiency of the contacting technique, the reaction temperature, and the desired degree of conversion, but will generally be in the range of from about 1 minute to about 10 hours, preferably in the range of about 30 minutes to about 5 hours. Generally, the reaction time is quite low since the cataysts of this invention are very active even at low temperatures. The dimerization can be carried out in a batch process or continuous process or even in a semi-continuous process wherein butadiene is intermittently charged as needed to replace that already dimerized. Generally, in a continuous dimerization process, the grams of conjugated diene per gram of iron triad catalyst per hour is in the range of about 3/1 to about 30,000/1, preferably about 1,000/1 to about 2,000/1. Any suitable reactor system can be employed. A very useful technique involves passing a solution of the iron triad metal nitrosyl halide along with the diolefin through a bed of particulate elemental Sn, Mn, or Zn metal.

At the end of the dimerization, the dimer can be recovered by any suitable conventional methods such as fractional distillation, solvent extraction, adsorption techniques, etc.

The dimerization process of this invention has particular utility in obtaining purer diolefin from a hydrocarbon fraction containing other hydrocarbons which boil at approximately the same temperature as the diolefin. For example, the dimerization is useful in the treatment of $C_4$ refinery streams which contain conjugated dienes such as 1,3-butadiene and other hydrocarbons boiling within about 30° F. of the boiling point of the 1,3-butadiene. The treatment typically would involve treating the $C_4$ fraction to eliminate deleterious amounts of acetylenes, 1,2-dienes, oxygen and water. Then the $C_4$ fraction would be subjected to dimerization in accordance with this invention. The dimerization product would then be separated into a first heavy fraction of vinylcyclohexene and materials of higher boiling point than vinylcyclohexane and a first light fraction of hydrocarbons of lower boiling point than vinylcyclohexene.

The first heavy fraction can then be separated by a technique such as steam stripping into a second heavy fraction of materials of higher boiling point than vinylcyclohexene and a second light fraction of vinylcyclohexene. The second light fraction, viz, vinylcyclohexene would be passed along with steam into a cracking zone wherein vinylcyclohexene would be converted into 1,3-butadiene. The effluent from the cracking zone could be cooled to recover a water phase which can be removed, converted into steam and reused in the cracking operation. After the condensed water is removed, the effluent from the cracking zone can be separated into a third heavy fraction containing vinylcyclohexene and materials having boiling points greater than vinylcyclohexene and a third light fraction containing materials having lower boiling points than vinylcyclohexene. The third heavy fraction can be recycled to the cracking zone. The third light fraction can be separated into a fourth light fraction containing 1,3-butadiene and materials having lower boiling points than 1,3-butadiene and a fourth heavy fraction of materials having boiling points greater than 1,3-butadiene. The fourth light fraction could then be separated into a fifth light fraction consisting of materials having boiling points lower than that of 1,3-butadiene and a fifth heavy fraction containing 1,3-butadiene in a more concentrated form than the original $C_4$ feed which is subjected to dimerization. Generally, in such a process the fifth light fraction and the fourth heavy fraction could be directed so that they could be added to the dimerization zone along with $C_4$ feed.

Of course the dimers obtained from the dimerization process of this invention can be isolated and used for other purposes which are well known in the art. For example, 4-vinylcyclohexene obtained from 1,3-butadiene can be converted to styrene or 1,2-bis(3-cyclohexene-1-yl)ethylene.

The preparation of iron triad metal nitrosyl halides and the use of those materials for dimerization both in accordance with this invention will be further illustrated by the following examples. In the following examples, the elemental metals employed had an average particle diameter in the range of about 0.074 mm to about 0.149.

EXAMPLE I

The runs of this example for the preparation of the iron nitrosyl halide according to the process of the invention utilized triphenyl phosphine as the ligand-forming compound in the iron nitrosyl halide preparation step. For convenience, the iron nitrosyl halide preparations in the examples will be identified by a catalyst number though it will be recognized that in the dimerization runs the additional metal catalyst component is also present in the dimerization catalyst.

Catalyst No. 1 was prepared by charging 3.1 grams (19.1 mmol) of ferric chloride, 1.2 grams (21.5 mg-atom) of iron powder, 6 grams (87 mmol) of sodium nitrite and 5 grams (19.1 mmol) of triphenyl phosphine to a 250 ml Schlenk flask. The flask was evacuated and 100 ml of tetrahydrofuran (THF) was added to the flask. The flask was heated at reflux for 3 hours, then cooled and filtered to obtain a dark brown/black filtrate. Said filtrate was allowed to stand overnight. The THF was removed from the filtrate under vacuum at room temperature to leave a black tarry material which was insoluble in pentane. After additional evacuation treatment, 100 ml of THF was added to the filtrate to provide a solution that was approximately 0.2 molar in iron. Said solution was stored under nitrogen at a low temperature.

Catalyst No. 2 was prepared by charging 1 gram (6.2 mmol) of ferric chloride, 0.68 grams (12.2 mg-atom) of iron powder, 1.60 grams (6.1 mmol) of triphenyl phosphine and 0.84 grams (12.2 mmol) of sodium nitrite to a 250 ml Schlenk flask. THF (40 ml) was added to the mixture and the resulting mixture heated for 2 hours at reflux. The mixture was allowed to stand overnight and then refluxed for an additional 1 hour. The reaction mixture was cooled and filtered to obtain a brown-black filtrate.

Catalyst No. 3 was prepared employing an excessive amount of triphenyl phosphine by charging 1 gram (6.2 mmol) of ferric chloride, 0.68 grams (12.2 mg-atom) of iron powder, 3.40 grams (13 mmol) of triphenyl phosphine and 0.7 grams (10.1 mmol) of sodium nitrite to a 100 ml Schlenk flask under a nitrogen atmosphere. THF (40 ml) was added to the mixture and the mixture heated at reflux with stirring for three hours. At the end of this time, it was cooled to room temperature and left to stand under nitrogen. The mixture was later filtered and the filtrate utilized as the catalyst component in a 1,3-butadiene dimerization run as described below.

Each of the nitrosyl iron chloride preparations described above were utilized in 1,3-butadiene dimerization reactions. The dimerization reactions were carried out in a Fisher-Porter aerosol compatibility bottle as the reaction vessel. In some of the runs, additional THF was added to the reactor as a diluent while in other runs no additional diluent was utilized in the dimerization reaction. Each of the reaction mixtures was analyzed by gas-liquid phase chromatography (GLC). The amounts of reactants and reaction conditions utilized in the butadiene dimerization runs as well as the results obtained in said runs are presented in Table I below. It will be noted that tin metal was utilized as the reducing agent for the nitrosyl iron chloride catalyst component in the dimerization runs.

Run No. 7 is believed to be due to presence of excess triphenyl phosphine in the nitrosyl catalyst charge.

EXAMPLE II

Other runs were carried out according to the instant invention in which the iron nitrosyl chloride component was prepared in the presence of triphenylphosphine oxide as the ligand-forming compound.

Catalyst No. 4 was prepared by charging 1 gram (6.2 mmol) of ferric chloride, 0.68 grams (12.2 mg-atom) of iron powder, 1.70 grams (6.1 mmol) of triphenylphosphine oxide and 0.7 grams (10.1 mmol) of sodium nitrite to a 100 ml Schlenk flask under a nitrogen atmosphere. THF (40 ml) was added to this mixture and the mixture heated at reflux with stirring for 3 hours. At the end of the 3 hour reaction period, the reaction was terminated and allowed to stand at room temperature overnight. An aliquot of the mixture was removed for isolation and examination of the solid and one-half of the remainder was placed in a tube under nitrogen for later use as catalyst. The aliquot portion was treated to remove the THF by vacuum and then benzene and heptane were added to give a semi-solid material. Evaporation of these liquids left a dark brown solid. This material was examined by infrared analysis which indicated the presence of two nitrosyl ligands whose absorption best fit those expected for the compound $Fe(NO)_2$(triphenylphosphine oxide)Cl.

Catalyst No. 5 was prepared in the same manner as that described for catalyst No. 4. After the reaction mixture had refluxed for 3 hours, the mixture was cooled and filtered and the filtrate retained for use in diene dimerization reactions.

Next a preparation was conducted on a larger scale than the two previous runs of the instant example. In this preparative run, there was added 10 grams (61.6 mmol) of ferric chloride, 7 grams (125.3 mg-atom) of iron powder, 17 grams (61.1 mmol) of triphenylphosphine oxide, and 7 grams (101.4 mmol) of sodium nitrite to a 500 ml Schlenk flask under a nitrogen atmosphere. THF (250 ml) was added to the mixture and stirred for 3 hours at room temperature. The mixture was then heated at reflux for 3 hours during which it became dark brown in color. The mixture was cooled for about 0.5 hours and then filtered through a medium porosity fritted glass filter and 220 ml of the solution was transferred to a sealed vessel under a nitrogen atmosphere. The remainder of the solution showed some olive colored solid precipitating out so it was cooled in a refrigerator for 3 days to facilitate the precipitation of the solid. Following this, the solvent was removed from the solution and the tarry remains were evacuated at about 25° C. under a pressure of $10^{-4}$ atmospheres for 1.5

TABLE I

| Run No. | Time, hr. | Temp., °C. | Catalyst (Fe) No. | mmol (a) | Sn, g(mg-atom) | THF, ml | Bd, g | 4-VCH % Yield (b) |
|---|---|---|---|---|---|---|---|---|
| 1 | 1.5 | 60 | 1 | 1.2 | 1.3 (11) | 0 | ca. 18 | ca. 80(c) |
| 2 | 5 | 50 | 1 | 1.0 | 0.7 (5.9) | 0 | 22.5 | 95 |
| 3 | 5 | 60 | 2 | 0.69 | 0.6 (5) | 8 | 17.1 | >90 |
| 4 | 5 | 60 | 2 | 0.69 | 0.5 (4.2) | 10 | 15.2 | 76 |
| 5 | 4 | 60 | 2 | 0.69 | 0.7 (5.9) | 10 | 16.4 | 89 |
| 6 | 5 | 60 | 2 | 0.69 | 0 | 10 | 5.5 | 0 |
| 7 | ca. 12 | 60 | 3 | 0.69 | 0.7 (5.9) | 10 | 14.4 | 0 |

Estimated value based on expected concentration of ferrous chloride from reaction of $FeCl_3$ with Fe(O) and optimum reaction of $FeCl_2$ with $NaNO_2$.
(b) Yield based on 1,3-butadiene charged to reaction mixture.
(c) Quantitative analysis not made.

The above results demonstrate that catalysts prepared according to the instant invention are active for the dimerization of 1,3-butadiene to 4-vinylcyclohexene in good yield. Run No. 6 demonstrates that without a reducing agent (Sn metal) the iron catalyst component is inactive for dimerization. The lack of dimerization in days. To this material 70 ml of THF were added and the resulting solution, which was brown/green in color, was stirred vigorously for 0.5 hours. The mixture was then treated with 40 ml of n-heptane added slowly under nitrogen while being stirred. A solid precipitate was recovered by filtration from the solution using a medium porosity fritted glass filter. The solid was ene. These runs utilized a variety of metals as reducing agents for the nitrosyl iron chloride catalyst component and in some instances, without additional THF being added to the reaction mixture. The results of said dimerization runs are presented below in Table II along with the reaction conditions employed and the amounts of the catalyst utilized.

TABLE II

| Run No. | Time, hr. | Temp., °C. | Catalyst (Fe) No. | mmol | Metal, (mg-atom) | THF, ml | Bd, g | 4-VOH % Yield(d) |
|---|---|---|---|---|---|---|---|---|
| 1 | ca. 16 | 60 | 4 | 0.69(a) | Sn(5) | 10 | 19 | 95 |
| 2 | ca. 16 | 60 | 5 | 0.46(a) | Sn(6.7) | 10 | 23 | ca. 100 |
| 3 | 5 | 60 | 6A | 0.35(b) | Sn(4.6) | 5 | 9.6 | (c) |
| 4 | 3.5 | 60 | 6B | 1.85(a) | Zn(7.6) | 5 | 17.2 | ca. 80 |
| 5 | 0.5 / 2 | 110 / 80 | 6B | 1.85(a) | Mn(18.2) | 5 | 25.1 | >50 |
| 6 | 1.5 | 65–70 | 7 | 0.7(b) | Sn(2.5) | 5 | 19.6 | ca. 100 |
| 7 | 18 | 65 | 8 | 0.7(b) | Zn(0.8) | 0 | 9.1 | ca. 95 |
| 8 | 2.5 | 65–70 | 8 | 0.7(b) | Sn(2.5) | 5 | 16.8 | ca. 100 |

(a)Estimated value based on expected concentration of ferrous chloride from reaction of $FeCl_3$ with Fe(O).
(b)Charged solid material believed to be: $Fe(NO)_2((phenyl)_3PO)Cl$.
(c) A large amount of 4-VCH was observed in the GLC analysis but no estimate of yield was made.
(d)Yield based on 1,3-butadiene charged to reaction mixture.

washed with 20 and 10 ml portions of n-pentane and dried under vacuum. Both the isolated solid material and the initial filtrate from the reaction mixture contain the active nitrosyl iron chloride catalyst component. The solid is here denoted Catalyst No. 6A and the filtrate Catalyst No. 6B.

Catalyst No. 7 was prepared utilizing the same amounts of reactants as in the preparation of catalyst No. 6 but with a slightly different reaction procedure. In this instance, the mixture with 200 ml THF was stirred for 0.5 hour at room temperataure and then for 3 hours at reflux. The mixture was filtered through a coarse porosity fritted glass filter while still hot. The solid material was precipitated from the THF solution by the addition of n-heptane. The precipitated solid was still tacky even after washing with n-pentane. Some inadvertent contact with air may have occurred with the solid while it was left overnight.

Catalyst No. 8 was prepared by charging 20 grams (123.3 mmol) of ferric chloride, 14 grams (250.7 mg-atom) of iron powder, 34 grams (122.2 mmol) of triphenylphosphine oxide, and 14 grams (202.9 mmol) of sodium nitrite to a 500 ml Schlenk flask under a nitrogen atmosphere. THF (250 ml) was added to this mixture under nitrogen and refluxed for 4 hours. The mixture was cooled and filtered. The filtrate was taken to dryness under vacuum and the remaining solid material was extracted with hot THF but only a small amount of material was apparently removed in this extraction step. THF (100 ml) was added to the residue remaining from the evaporated filtrate and there was produced a dark brown solution to which was added 100 ml of n-heptane with additional stirring. This mixture was then evaporated with cooling to precipitate a solid material and then filtered. The solid was then washed with n-pentane until the pentane washings were colorless. The solid material obtained in this filtration step was dried under vacuum to give 34.5 grams of dark brown solid. The extracted residue from the original reaction mixture was also recovered and it weighed 38 grams. Presumably this residue material contained very little THF as a compound or in combination with the nitrosyl halide as a ligand.

The catalyst materials prepared as described were utilized in a number of dimerization runs for 1,3-butadi-

EXAMPLE III

In a control run, the following reaction mixture was prepared in a Fisher-Porter aerosol compatibility bottle: 0.25 grams (1.5 mmol) of ferric chloride, 0.3 grams (2.5 mg-atom) of tin powder and 0.3 grams (4.5 mmol) of sodium nitrite. The bottle reactor was evacuated then flushed with nitrogen followed by the addition of 10 ml of THF. The mixture was cooled with dry ice and 18.3 grams (339 mmol) of 1,3-butadiene added. This reaction mixture was heated to 75° C. with stirring. During this time, the original dark green solution changed in color to an orange-brown color. After 5 hours, the reaction was terminated and the reaction mixture allowed to cool to room temperature and stand for 1 day. Pressure on the reactor was still at 25 psig indicating there had been little, if any, conversion of 1,3-butadiene to the dimer. The results of this run indicate that one does not obtain dimerization of 1,3-butadiene to 4-vinylcyclohexene if one attempts to form the iron nitrosyl halide simultaneously with the dimerization.

EXAMPLE IV

Catalyst No. 6B of Example II above was utilized in a series of runs for the dimerization of butadiene with elemental tin as a reducing agent in the presence of added olefinic compounds such as isobutylene and cis-2-butene.

In run No. 1 of this example, a Fisher-Porter aerosol compatibility bottle was charged with 2 ml (ca. 0.74 mmol) of the nitrosyl iron chloride catalyst component No. 6B, 5 ml of THF, 0.9 grams (7.6 mg-atom) of tin powder, 9.5 grams (176 mmol) of 1,3-butadiene and 8.1 grams (145 mmol) of isobutylene. The above reaction mixture was heated at 60° C. for 5 hours and then allowed to cool and stand overnight. Later, 1 ml of n-undecane was added to the reaction vessel to use as an internal standard for gas-liquid phase chromatography (GLC) analysis. Although reliable quantitative analysis results were not obtained in this run, it was apparent that the catalyst system was active for the dimerization of 1,3-butadiene in the presence of large amounts of isobutylene.

Run No. 2 of the instant example was carried out by charging a Fisher-Porter aerosol compatibility bottle with 2 ml (ca. 0.74 mmol) of the nitrosyl iron chloride catalyst component No. 6B, 5 ml of THF, 0.6 grams (5 mg-atom) of tin powder, 13.5 grams (250 mmol) of 1,3-butadiene and 9.9 grams (177 mmol) of cis-2-butene. The reaction mixture was treated in the same manner as that described for run No. 1 of this example. In this run GLC analysis indicated a 70% yield of the 4-vinylcyclohexene dimer based on the amount of 1,3-butadiene charged. This result also indicated that the catalyst system described was active for the dimerization of 1,3-butadiene to 4-vinylcyclohexene in the presence of large amounts of cis-2-butene.

Run No. 3 was carried out by charging a Fisher-Porter aerosol compatibility bottle with 2 ml (ca. 0.74 mmol) of the nitrosyl iron chloride catalyst component No. 6B, 5 ml of THF, 0.6 grams (5 mg-atom) of tin powder, and 12.4 grams (230 mmol) of 1,3-butadiene. This mixture was treated in essentially the same manner as the previous two runs of this series. Gas-liquid phase chromatography analysis showed a 96% yield of 4-vinylcyclohexene from 1,3-butadiene in this run. The apparent high yield of the dimer in the latter run compared to the previous two runs indicate that dimer yield may be somewhat lower when the dimerization reaction is carried out in the presence of olefinic compounds such as isobutylene or cis-2-butene.

EXAMPLE V

Another dimerization run with the iron nitrosyl chloride catalyst component No. 6B of Example II was carried out. In this dimerization run, the 1,3-butadiene was present in admixture with several other C$_4$ hydrocarbons to simulate a refinery C$_4$ stream. The composition of the synthetic C$_4$ stream was as follows:

| Stream Component | Weight, % |
|---|---|
| Isobutane | 2.26 |
| Isobutene | 27.73 |
| Cis-2-butene | 5.03 |
| n-Butane | 5.02 |
| Trans-2-butene | 7.17 |
| 1-Butene | 16.49 |
| 1,3-Butadiene | 36.30 |

In the instant run, a Fisher-Porter aerosol compatibility bottle was charged with 5 ml (ca. 1.85 mmol) of catalyst component No. 6B, 5 ml of THF, 0.7 grams (5.9 mg-atom) of tin metal powder and 19.6 grams (132 mmol 1,3-butadiene) of the above-described C$_4$ hydrocarbon mixture. The above-described reaction mixture was heated to 65° C. with stirring for 24 hours. After standing at room temperature for 1 week, 2 ml of n-undecane was added to the mixture as an internal standard for GLC analysis. Two analyses showed the presence of 4-vinylcyclohexene in 88.72% yield in one analysis and 92.69% yield in the second analysis. The yield figures are based upon the amount of 1,3-butadiene in the original reaction mixture. These results indicate that the catalyst was quite active toward dimerization of 1,3-butadiene in the presence of other C$_4$ hydrocarbons, such as might be found in a typical refinery C$_4$ stream.

EXAMPLE VI

Catalyst No. 9 was prepared to demonstrate the preparation of an active catalyst without the addition of a ligand-forming compound other than the ether (tetrahydrofuran) utilized in the preparation step. In this run, there was added 5 grams (30.8 mmol) of ferric chloride and 1 gram (17.9 mg-atom) of iron powder to a 500 ml Schlenk flask followed by the addition of 100 ml of THF under a nitrogen atmosphere. This mixture was stirred under reflux conditions until the solution turned from its original red-brown color to gray, which indicated the production of the ferrous halide. Then, there was added to the reaction vessel 2.2 grams (31.9 mmol) of sodium nitrite and the mixture stirred under reflux for two hours. The mixture was allowed to stand at room temperature overnight with stirring.

Dimerization of 1,3-butadiene present in a synthetic C$_4$ stream having the same composition as that employed in Example V was conducted by charging 10 ml (ca. 4.62 mmol) of catalyst No. 9, 0.35 grams (5.4 mg-atom) of zinc powder and 31.2 grams of a C$_4$ stream which contained 11.326 grams (210 mmol) of 1,3-butadiene. The temperature of the mixture was increased from 15° C. to 55° C. over a 4-hour period and allowed to cool at room temperature. There was added to the mixture 1.6 grams of dodecane as an internal standard for gas-liquid phase chromatography (GLC) analysis. Said analysis indicated the presence of 9.24 grams of 4-vinylcyclohexene for a yield of 81.6% based on the 1,3-butadiene present in the original reaction mixture.

A second run was carried out by utilizing 5 ml (ca. 2.31 mmol) of the catalyst No. 9, 0.35 grams (5.4 mg-atom) of zinc powder, 0.2 grams of potassium iodide and 22.7 grams (420 mmol) of 1,3-butadiene. The reaction was carried out over a period of about 2½ hours with the temperature being increased 21°–50° C. At the conclusion of the reaction, the mixture was allowed to cool and 1.65 grams of dodecane was added to the mixture as an internal standard for GLC analysis. Said analysis indicated the presence of 19.628 grams of 4-vinylcyclohexene for a yield of 86.5% based on the 1,3-butadiene charged to the reaction mixture. It is not believed that the presence of the potassium iodide had any significant effect on the yield of the 4-vinylcyclohexene produced in the instant run.

EXAMPLE VII

A run was carried out charging an amount of tin powder sufficient for the dimerization reaction to a mixture comprising the ferric chloride, triphenylphosphine oxide, and sodium nitrite in THF. The run was carried out by charging 5 grams (30.8 mmol) of ferric chloride, 7 grams (59 mg-atom) of tin powder, 8.5 grams (30.5 mmol) of triphenylphosphine oxide and 3.5 grams (50.7 mmol) of sodium nitrite and 100 ml of THF to a 200 ml Schlenk flask. The mixture was refluxed for 3 hours during which time the mixture changed color from a dark green to a dark red-brown which is characteristic of the nitrosyl iron chloride complex with triphenylphosphine oxide as a ligand.

The above mixture was tested for its dimerization activity by charging 5 ml of the reaction mixture with 5 ml of additional THF and 8.5 grams (157 mmol) of 1,3-butadiene to a Fisher-Porter aerosol compatibility bottle. This mixture was heated to 60° C. with stirring overnight. Analysis of the mixture by gas-liquid phase chromatography showed the presence of a substantial amount of 4-vinylcyclohexene. No attempt was made to determine the quantitative yield of the cyclic dimer. This result, however, does demonstrate that a one-step preparation of the dimerization catalyst is possible.

A portion of the one-step catalyst preparation described above was taken to dryness and 0.6 grams of this solid material was utilized for the dimerization of 1,3-butadiene (12.7 grams, 235 mmol) in 10 ml of THF. The mixture of catalyst, solvent, and 1,3-butadiene was stirred in a Fisher-Porter aerosol compatibility bottle at 60° C. for 5 hours. Essentially no change in the pressure on the vessel was noted during this reaction time. The mixture was allowed to stand overnight at room temperature (ca. 23° C.) and 0.74 grams of n-undecane added to the mixture as an internal standard for GLC analysis. Said analysis indicated only a small amount of 4-vinylcyclohexene was present. Close examination of the remaining solid from the one-step catalyst preparation indicated that it had been oxidized, probably by accidental contact with air. This is expected to have been the reason for the low yield of 4-vinylcyclohexene in the dimerization reaction.

EXAMPLE VIII

Catalyst No. 10 was prepared according to the instant invention wherein ferrous chloride ($FeCl_2$) was reacted directly with sodium nitrite in the presence of tetrahydrofuran (THF) to produce the iron nitrosyl chloride catalyst component. In this run, a 100 ml Schlenk flask was charged with 1 gram (7.9 mmol) of ferrous chloride which had been previously dried by heating under reduced pressure, 2 grams (29 mmol) of sodium nitrite and 30 ml of THF. The resulting dark green solution was stirred under nitrogen at reflux temperature of the THF and after about 0.5 hours, the solution had become dark brown. Refluxing of the reaction mixture was continued for a total of 1.5 hours.

A Fisher-Porter aerosol compatibility bottle was charged with 1 ml of catalyst No. 10 reaction mixture (equivalent to 0.26 mmol of ferrous iron), 0.3 grams (4.6 milligram atoms) of zinc powder, 10 ml THF and 14.2 grams (263 mmol) of 1,3-butadiene. The dimerization reaction mixture was stirred while heating to a temperature of about 70° C. in about 1 hour and stirring was continued while the temperature was then allowed to cool to room temperature over a period of about 1 hour after which there was added 1.58 grams of n-dodecane as an internal standard for gas-liquid phase chromatography analysis. The GLC analysis indicated a 106% yield of 4-vinylcyclohexene had been obtained in the dimerization run. This yield figure indicated a possible weighing error had been made but in any event demonstrated that catalyst No. 10, which had been prepared directly by the reaction of ferrous chloride with sodium nitrite in THF, was a very active catalyst component for the dimerization of 1,3-butadiene to 4-vinylcyclohexene.

EXAMPLE IX

Catalyst No. 11 was prepared according to the instant invention wherein a 500 ml Schlenk flask was charged with 8 grams (49 mmol) of anhydrous ferric chloride, 6 grams (107 mmol) of iron powder and 11 grams (159 mmol) of sodium nitrite. The flask was also charged with 250 ml of distilled 4-vinylcyclohexene as the reaction diluent and a stirring means (magnetic stirring bar). The reaction utilizing the above components was carried out by adding the ferric chloride and iron powder to the 4-vinylcyclohexene first and refluxing this mixture for 1 hour followed by the addition of sodium nitrite. The resulting mixture was refluxed for two additional hours. It was observed that the mixture at this time was essentially the same color as that observed for the preparation of the iron nitrosyl chloride catalyst in tetrahydrofuran solvent. At the end of the 3-hour reaction period, the solution was cooled and filtered. A large amount of unreacted or insoluble solid material was recovered. Presumably, this relatively large amount of recovered solid material was due to the poorer solvating ability of the 4-vinylcyclohexene in comparison to previously utilized tetrahydrofuran.

The activity of the above-described catalyst No. 11 in the dimerization of 1,3-butadiene was examined by charging 2 ml of said filtered solution (about 1.8 mmol Fe) with 0.7 grams of zinc powder and 20 grams of 1,3-butadiene to a Fisher-Porter aerosol compatibility bottle. This dimerization reaction mixture was maintained at 65°–70° C. for 2 hours after which analysis by gas-liquid phase chromatography of said dimerization reaction mixture showed a greater than 85% conversion of the 1,3-butadiene to 4-vinylcyclohexene. The exact amount of conversion could not be readily determined in the analysis because of the added 4-vinylcyclohexene in the catalyst component solution.

The results of the above-described dimerization of 1,3-butadiene indicate that the iron nitrosyl chloride prepared as described above in the absence of any liquid or ligand-forming compound was active as a 1,3-butadiene dimerization catalyst component.

EXAMPLE X

Another catalyst (No. 12) was prepared by reacting ferric chloride, iron powder and sodium nitrite in the presence of triphenylphosphine oxide for the production of an iron nitrosyl chloride. See previous runs of Example II for catalyst preparations utilizing triphenylphosphine oxide as the ligand-forming compound. The catalyst was prepared by charging $FeCl_3$, 4 g (24.6 mmol) and 100 ml tetrahydrofuran (THF) to a 200 ml Schlenk flask equipped with stirring means. To the stirred mixture of $FeCl_3$ and THF was added Fe powder, 2.8 g (50.1 mg-atoms), $NaNO_2$, 2.8 g (40.6 mmol), and triphenylphosphine oxide, 6.8 g (24.4 mmol). The resulting mixture was stirred at about 25° C. for 15 minutes then heated at reflux temperature (about 65° C.) for 3 hours under a nitrogen atmosphere. The mixture was cooled and transferred to a dried beverage bottle under nitrogen. The bottle was capped, flushed with nitrogen through the cap having a self-sealing rubber liner, and stored under nitrogen.

Catalyst No. 12 was utilized in a dimerization run employing isoprene as the conjugated diene reactant. In this run a Fisher-Porter aerosol compatibility bottle (177 ml) was charged with 0.7 g (5.9 mg-atoms) of tin powder, 5 ml (about 2.5 mmol Fe) of catalyst No. 12 preparation and 20 ml (13.62 g) of isoprene. The dimerization run was allowed to react at 65° C. overnight (about 16 hours). At the end of the run, the reactor was cooled and vented. The liquid products were analyzed by gas-liquid phase chromatography after 2 ml of n-undecane had been added as an internal standard for the analysis. The analysis showed 82% conversion of isoprene with an 88% selectivity to one dimer (apparently limonene) and an overall 98% selectivity to all dimeric species.

The results of the isoprene dimerization run carried out with the catalyst according to the instant invention demonstrate that isoprene is very readily converted to the dimeric species according to the instant invention.

Although this invention has been described in considerable detail, it must be understood that such detail is for the purpose of illustration and that many variations and modifications can be made by one skilled in the art without departing from the spirit and scope of the invention herein disclosed and claimed.

What is claimed is:

1. A catalyst system formed by contacting components consisting essentially of (1) at least one elemental metal selected from the group consisting of manganese, tin, and zinc with (2) at least one nitrosyl metal halide selected from the group consisting of nitrosyl metal halides having the formulas $[Fe(NO)_2X]_y$, $[Co(NO)_2X]_y$, $[Ni(NO)X]_y$, $Fe(NO)_2(L)X$, $Ni(NO)(L)X$, and $Co(NO)_2(L)X$, wherein X is selected from the group consisting of chloride, bromide, and iodide, y is 1 or 2 for Co and Fe and 1, 2, 3, or 4 for Ni, and wherein (L) is selected from the group of compounds having the formulas $$R_3M, (RO)_3M, SR', R-S-R, R_3MO, OR', \text{ and } R-O-R$$

wherein each R is individually selected from the group consisting of hydrocarbyl aromatic radicals, hydrocarbyl aliphatic radicals, halo-substituted hydrocarbyl aromatic radicals, halo-substituted aliphatic hydrocarbyl radicals, alkoxy-substituted hydrocarbyl aromatic radicals and alkoxy-substituted aliphatic hydrocarbyl radicals having up to about 20 carbon atoms, wherein R' is a divalent saturated or olefinically unsaturated hydrocarbyl radical having 3 to 7 carbon atoms, and wherein M is phosphorus, antimony, or arsenic.

2. A catalyst system according to claim 1 wherein the mole ratio of said elemental metal to said nitrosyl metal halide is in the range of about 0.75/1 to about 50/1 and said elemental metal is a powder.

3. A catalyst system according to claim 2 wherein the nitrosyl metal halide is an iron nitrosyl halide.

4. A catalyst system according to claim 3 wherein said iron nitrosyl halide is selected from the group consisting of compounds having the formulas $[Fe(NO)_2Cl]_y$ or $Fe(NO)_2(L)Cl$, wherein L is selected from the group consisting of tetrahydrofuran, triphenylphosphine, and triphenylphosphine oxide.

5. A catalyst system according to claim 1 formed by contacting said at least one elemental metal with the reaction product mixture produced when an iron triad metal dihalide selected from the group consisting of iron dihalide and cobalt dihalide, wherein the halide is selected from the group consisting of chloride, bromide, and iodide, is reacted with at least one alkali metal nitrite in a liquid in which said iron triad metal dihalide is at least partially soluble, under reaction conditions suitable for yielding a corresponding iron triad metal nitrosyl halide.

6. A catalyst system according to claim 5 wherein said iron triad metal dihalide is reacted with said at least one alkali metal nitrite in the presence of a compound (L) which forms a ligand with said nitrosyl halide.

7. A catalyst system according to claim 6 wherein said iron triad metal dihalide is iron dichloride.

8. A catalyst system according to claim 1 formed by contacting said at least one elemental metal with the reaction product mixture produced when an iron triad metal dihalide selected from the group consisting of iron dihalide, cobalt dihalide, and nickel dihalide, wherein the halide is selected from the group consisting of chloride, bromide, and iodide, is reacted with at least one alkali metal nitrite in a liquid in which said metal dihalide is at least partially soluble and in the presence of at least one elemental metal selected from the group consisting of the corresponding iron triad metal and zinc, under reaction conditions suitable for yielding a corresponding iron triad metal nitrosyl halide.

* * * * *